United States Patent
Wan et al.

(10) Patent No.: US 12,214,127 B2
(45) Date of Patent: Feb. 4, 2025

(54) CALIBRATION METHOD FOR OXYGEN SENSOR, MEDICAL VENTILATION SYSTEM, ANESTHETIC MACHINE, AND VENTILATOR

(71) Applicant: SHENZHEN MINDRAY BIO-MEDICAL ELECTRONICS CO., LTD., Shenzhen (CN)

(72) Inventors: Congying Wan, Shenzhen (CN); Guangtao Chen, Shenzhen (CN); Wei Ling, Shenzhen (CN); Chao Wang, Shenzhen (CN); Dongsheng Liang, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 217 days.

(21) Appl. No.: 17/854,093

(22) Filed: Jun. 30, 2022

(65) Prior Publication Data

US 2022/0331533 A1  Oct. 20, 2022

Related U.S. Application Data

(63) Continuation of application No. PCT/CN2019/130214, filed on Dec. 30, 2019.

(51) Int. Cl.
*A61M 16/00* (2006.01)
*A61M 16/01* (2006.01)
(Continued)

(52) U.S. Cl.
CPC .......... *A61M 16/024* (2017.08); *A61M 16/01* (2013.01); *G01N 27/409* (2013.01);
(Continued)

(58) Field of Classification Search
CPC .... A61M 16/12; A61M 16/024; A61M 16/01; A61M 2205/3317; A61M 2205/70;
(Continued)

(56) References Cited

U.S. PATENT DOCUMENTS 8,776,791 B2 * 7/2014 Huang ................ A61M 16/024
                                             128/205.24
10,046,129 B2 * 8/2018 Haggblom .......... A61M 16/024
(Continued)

FOREIGN PATENT DOCUMENTS

CN  102012395 A  4/2011
CN  102441213 A  5/2012
(Continued)

OTHER PUBLICATIONS

International Search Report issued in corresponding International Application No. PCT/CN2019/130214, mailed Sep. 27, 2020, 6 pages.
(Continued)

*Primary Examiner* — An H Do
(74) *Attorney, Agent, or Firm* — BAYES PLLC

(57) ABSTRACT

A calibration method for an oxygen sensor and a medical ventilation system are disclosed. At least two electrical signals are acquired at two time points within a preset time period, when the oxygen sensor is in a preset oxygen concentration. A response function of the oxygen sensor which corresponds to the preset oxygen concentration, is determined according to the at least two time points and the at least two electrical signals. A steady-state output value of the oxygen sensor in the preset oxygen concentration is determined, according to the response function and a characteristic curve of the oxygen sensor is determined, according to the steady-state output value of the oxygen sensor in the preset oxygen concentration. The described method
(Continued)

reduces the time waiting for the oxygen sensor to respond, thus improving calibration efficiency, and facilitating the improvement of the oxygen concentration monitoring accuracy of a ventilation device in daily use.

11 Claims, 5 Drawing Sheets

(51) Int. Cl.
*A61M 16/10* (2006.01)
*G01N 27/409* (2006.01)
*G01N 27/417* (2006.01)

(52) U.S. Cl.
CPC . *G01N 27/4175* (2013.01); *A61M 2016/1025* (2013.01); *A61M 2205/3317* (2013.01); *A61M 2205/3334* (2013.01); *A61M 2205/702* (2013.01); *G01N 2201/127* (2013.01)

(58) Field of Classification Search
CPC .. A61M 2016/0027; A61M 2205/3334; A61M 2205/502; A61M 2205/702; A61M 2016/003; A61M 2016/1025; A61M 2202/0208; A61M 2202/0007; G01N 2201/127; G01N 27/409; G01N 27/4175
See application file for complete search history.

(56) References Cited

U.S. PATENT DOCUMENTS

| | | | |
|---|---|---|---|
| 11,229,763 B2* | 1/2022 | Oddo | A61M 16/0051 |
| 11,925,756 B2* | 3/2024 | Wan | G16H 40/60 |

FOREIGN PATENT DOCUMENTS

| | | |
|---|---|---|
| CN | 104215677 A | 12/2014 |
| CN | 104784793 A | 7/2015 |
| CN | 107084034 A | 8/2017 |
| JP | 10104190 A | 4/1998 |
| WO | 2009058081 A1 | 5/2009 |
| WO | 2009058083 A1 | 5/2009 |

OTHER PUBLICATIONS

Notice of allowance issued in related Chinese Application No. 201980098615.3, mailed Jul. 19, 2023, 5 pages.

* cited by examiner

Determining a model parameter of the response function of the oxygen sensor which corresponds to the preset oxygen concentration, according to the at least two time points and the at least two electrical signals — S121

Obtaining the response function of the oxygen sensor which corresponds to the preset oxygen concentration, according to the determined model parameter. — S122

FIG. 4

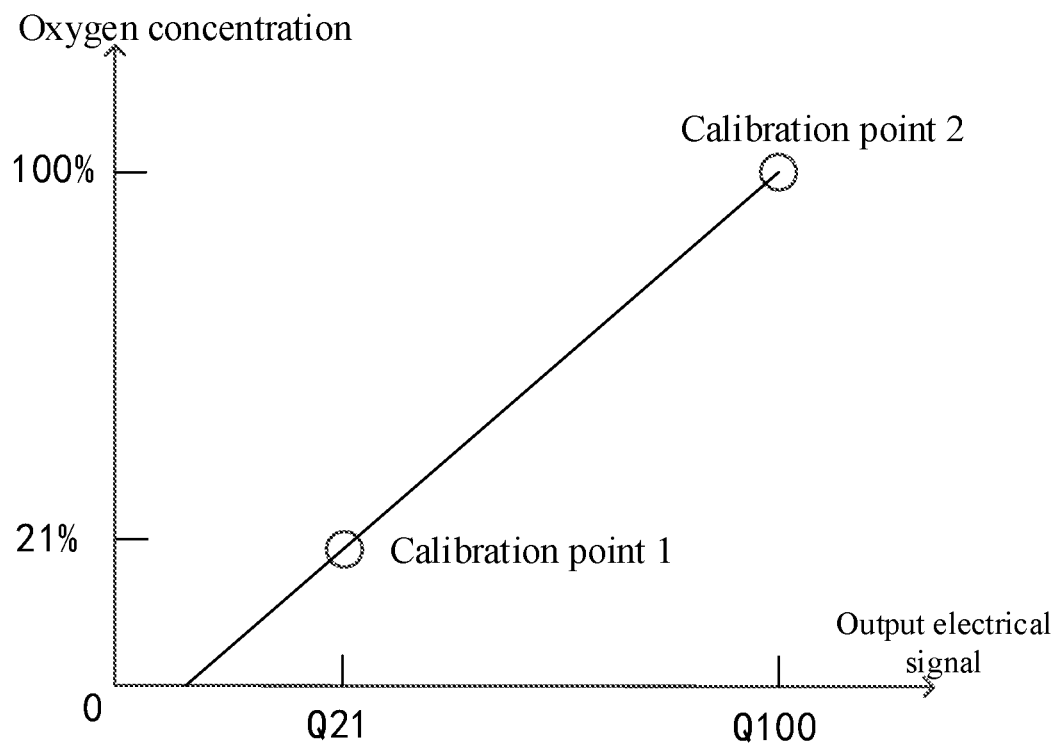

FIG. 5

CALIBRATION METHOD FOR OXYGEN SENSOR, MEDICAL VENTILATION SYSTEM, ANESTHETIC MACHINE, AND VENTILATOR

CROSS REFERENCE OF RELATED APPLICATIONS

This application is a continuation of Patent Cooperation Treaty Application No. PCT/CN2019/130214, filed on Dec. 30, 2019, which is hereby incorporated by reference in its entirety.

TECHNICAL FIELD

The disclosure relates to the technical field of oxygen sensors, and more particularly to a calibration method for an oxygen sensor, a medical ventilation system, an anesthetic machine, and a ventilator.

BACKGROUND

Medical ventilation systems, such as ventilators or anesthetic machines usually place oxygen sensors on the inspiratory branch to monitor inhaled oxygen concentration of the patient. Common oxygen sensors include electrochemical oxygen cells and paramagnetic oxygen sensors. The principle of electrochemical oxygen cell is that the voltage value which is generated by the oxygen cell is proportional to the oxygen concentration under fixed pressure and temperature. The oxygen concentration of the mixed gas can be calculated by acquiring the voltage-oxygen concentration proportional coefficient of the oxygen cell under the operation pressure and temperature through calibration operation and monitoring the voltage output of the oxygen cell in the mixed gas.

As the electrochemical reaction of the oxygen cell is a consumption process, the outputted voltage-oxygen concentration proportional relationship may change with time, so it is necessary to conduct calibration operation every other period of time to determine the voltage-oxygen concentration proportional coefficient again.

Oxygen cell calibration is a maintenance function that is often used in the usage of ventilator/anesthetic machine. It is generally recommended to implement 100% and 21% oxygen concentration calibration at least once a month, and implement 21% oxygen concentration calibration at least once every 72 hours. For accurate monitoring of daily use, it is preferable to implement 21% oxygen concentration calibration every 24 hours, which is a high calibration frequency. However, at present, the calibration process of oxygen cell takes a long time, and the calibration of a single point takes 3 to 5 mins. This is because the response of the electrochemical oxygen cell is slow. When environment abruptly changes, such as from 21% oxygen concentration to 100% pure oxygen concentration, the oxygen cell needs about 3 mins to reach the maximum value stably. When the environment changes from 100% pure oxygen concentration to 21% oxygen concentration of pure air, the oxygen cell needs 3 to 5 minutes to reach the minimum value stably. The high-frequency calibration and the long calibration time increase the additional machine preparation time, which undoubtedly increases the workload for the busy medical work.

SUMMARY

In this regard, a calibration method for an oxygen sensor, a medical ventilation system, an anesthetic machine, and a ventilator, are provided in this disclosure, which are capable of calibrating a characteristic curve of the oxygen sensor.

In a first aspect, the embodiment of this disclosure provides a calibration method for an oxygen sensor, which including:
acquiring at least two electrical signals, which are correspondingly outputted by the oxygen sensor at at least two time points within a preset time period, when the oxygen sensor is in a preset oxygen concentration;
determining a response function of the oxygen sensor which corresponds to the preset oxygen concentration, according to the at least two time points and the at least two electrical signals, wherein the response function represents a relationship between the electrical signal, which is outputted by the oxygen sensor, and time;
determining a steady-state output value of the oxygen sensor in the preset oxygen concentration, according to the response function;
determining a characteristic curve of the oxygen sensor, according to the steady-state output value of the oxygen sensor in the preset oxygen concentration.

In a second aspect, the embodiment of this disclosure provides a medical ventilation system, which including at least one gas source interface, at least one gas supply branch which is connected with the at least one gas source interface, and a respiratory line;
the respiratory line includes an inspiratory branch which is provided with an oxygen sensor;
the at least one gas supply branch is configured to output a gas to the inspiratory branch;
wherein the medical ventilation system further includes a processor which is configured to implement following steps:
controlling the at least one gas supply branch to output the gas to the inspiratory branch to adjust to a preset oxygen concentration of gas inside the inspiratory branch;
acquiring at least two electrical signals, which are correspondingly outputted by the oxygen sensor at at least two time points within a preset time period, when the oxygen sensor is in the preset oxygen concentration;
determining a response function of the oxygen sensor which corresponds to the preset oxygen concentration, according to the at least two time points and the at least two electrical signals, wherein the response function represents a relationship between the electrical signal, which is outputted by the oxygen sensor, and time;
determining a steady-state output value of the oxygen sensor in the preset oxygen concentration, according to the response function;
determining a characteristic curve of the oxygen sensor, according to the steady-state output value of the oxygen sensor in the preset oxygen concentration.

In a third aspect, the embodiment of this disclosure provides an anesthetic machine, which including the aforementioned medical ventilation system.

In a fourth aspect, the embodiment of this disclosure provides a ventilator, which including the aforementioned medical ventilation system.

The embodiments of this disclosure have provided a calibration method for an oxygen sensor, a medical ventilation system, an anesthetic machine, and a ventilator. In which, at least two electrical signals, which are correspondingly outputted by the oxygen sensor at at least two time points within a preset time period when the oxygen sensor is in a preset oxygen concentration, are acquired. Then a response function of the oxygen sensor, which corresponds to the preset oxygen concentration, is determined. As the response function represents a relationship between the electrical signal, which is outputted by the oxygen sensor, and time, a steady-state output value of the oxygen sensor in the preset oxygen concentration can be determined according to the response function. In this way, a characteristic curve of the oxygen sensor can be determined according to the steady-state output value of the oxygen sensor in the preset oxygen concentration. It is just necessary to acquire at least two electrical signals in a short time after the change of ambient oxygen concentration, then the relationship between the electrical signals outputted by the oxygen sensor and time can be determined. Thus, the electrical signal, which is outputted by the oxygen sensor in a steady state in the corresponding oxygen concentration, can be correspondingly acquired, without waiting a long time for the voltage to be completely stable. Accordingly, the waiting responding time of the oxygen sensor can be reduced, the calibration efficiency can be improved, and it is convenient to improve the oxygen concentration monitoring accuracy of ventilation device, such as anesthetic machine or ventilator.

It should be understood that the above general description and the following detailed description are only exemplary and explanatory, and do not limit the disclosure of this specification.

BRIEF DESCRIPTION OF THE DRAWINGS

In order to explain embodiments of this disclosure or technical solutions in the prior art more clearly, the following will briefly introduce drawings required in the description for the embodiments or the prior art description. It is obvious that the drawings in the following description are only some embodiments of this disclosure. For those skilled in the art, other drawings can be obtained from these accompanying drawings without paying any creative works.

FIG. 4 is a schematic diagram of a sub-process of determining a response function in FIG. 1.

FIG. 5 is a schematic diagram for determining a characteristic curve of the oxygen sensor according to a calibration point.

REFERENCE NUMBERS

100. Medical ventilation system; 110. Gas source interface; 120. Gas supply branch; 130. Respiratory line; 131. Inspiratory branch; 10. Oxygen sensor; 132. Expiratory branch; 140. Gas control device; 101. Processor.

DETAILED DESCRIPTION

The technical solutions in example embodiments of the disclosure will be described clearly and completely below with reference to the accompanying drawings. Apparently, the embodiments described are merely some, rather than all, of the embodiments of the disclosure. It should be understood that the disclosure is not limited by the example embodiments described herein. All other embodiments derived by those skilled in the art without creative efforts on the basis of the embodiments described in the disclosure shall fall within the scope of protection of the disclosure.

The flow chart shown in the attached drawings is only an example and does not necessarily include all contents and operations/steps, nor must be executed in the described sequence. For example, some operations/steps can be disassembled, combined or partially combined, so the actual execution sequence may change according to the actual situation.

Some embodiments of this disclosure will be described in detail below in combination with the accompanying drawings. The following embodiments and features in the embodiments may be combined with each other without conflict.

Figure 1:
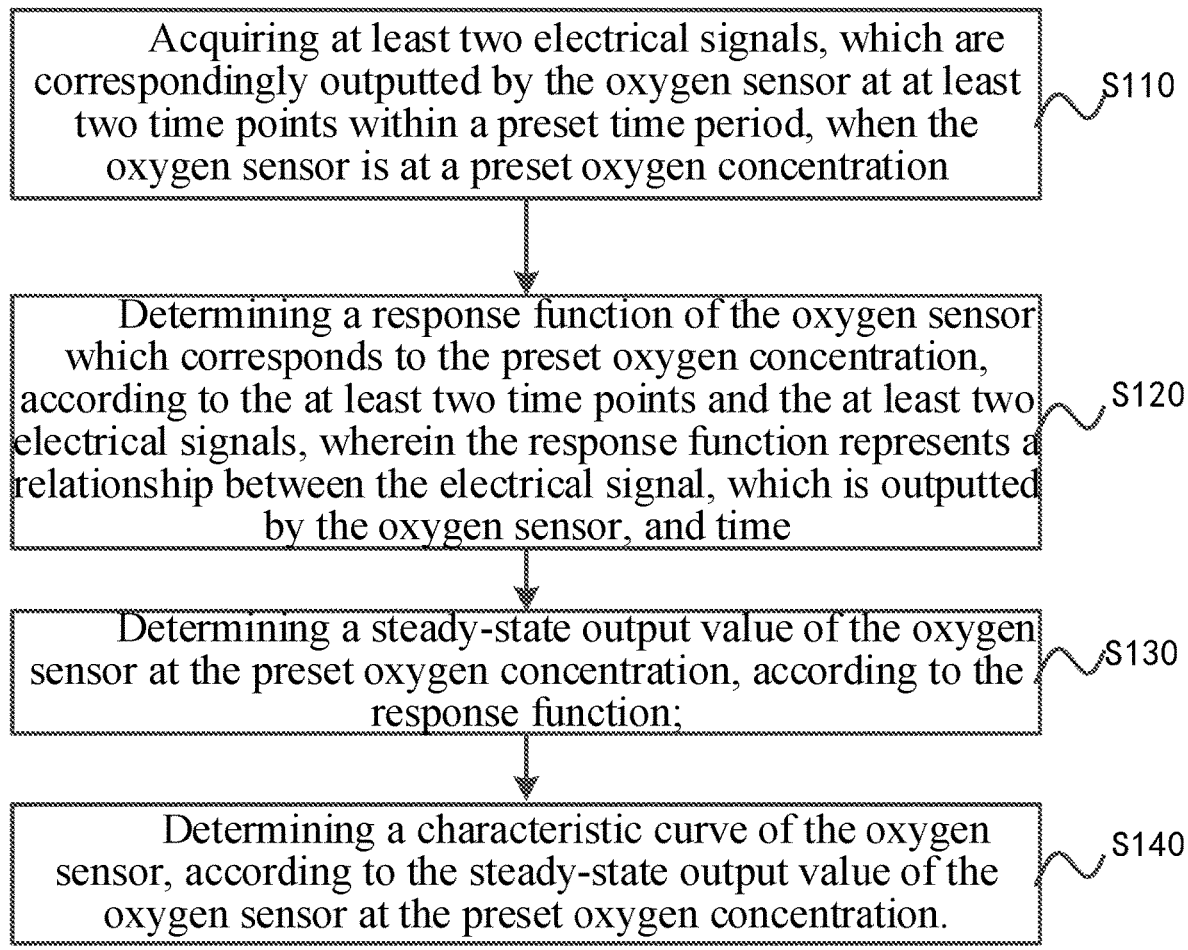
FIG. 1 is a flowchart of a calibration method for an oxygen sensor, in an embodiment of this disclosure.

FIG. 1 is a flowchart of a calibration method for an oxygen sensor, in an embodiment of this disclosure. Referring FIG. 1, this calibration method can be applied to a calibration device of the oxygen sensor, an oxygen concentration measurement device with the oxygen sensor, and the likes, for determining a characteristic curve of the oxygen sensor.

The calibration device of the oxygen sensor, the oxygen concentration measurement device with the oxygen sensor, and the likes, can include at least one of a medical ventilation system, tablet computer, notebook computer, desktop computer, personal digital assistant, wearable device, etc. Further, the medical ventilation system may be a medical ventilation system in an anesthetic machine or a ventilator.

Figure 2:
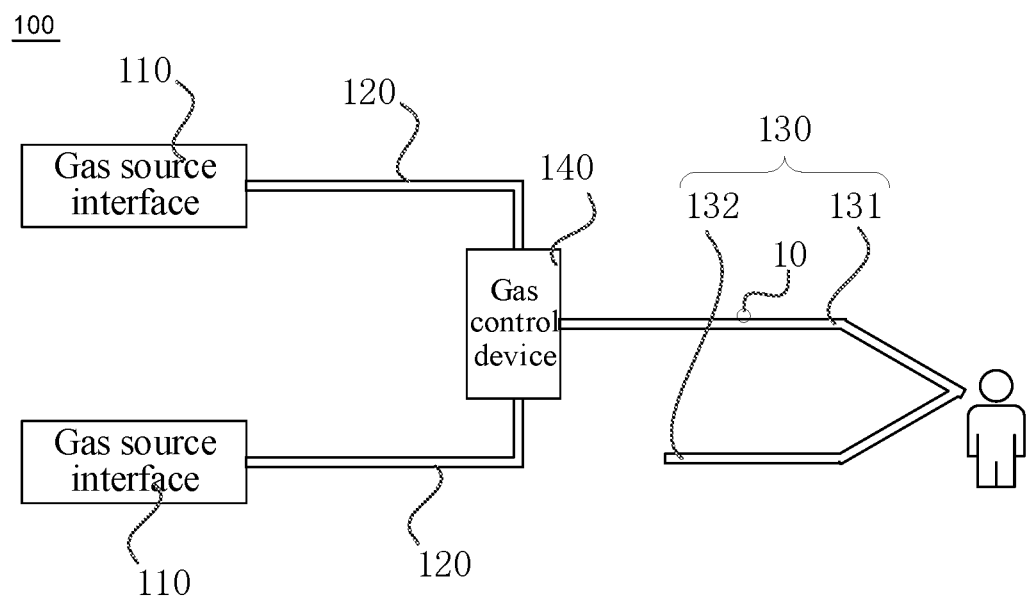
FIG. 2 is a structural diagram of a medical ventilation system.

For example, as shown in FIG. 2, the medical ventilation system 100 includes at least one gas source interface 110, at least one gas supply branch 120 which is connected with the at least one gas source interface 110, and a respiratory line 130.

The respiratory line 130 includes an inspiratory branch 131 which is provided with an oxygen sensor 10.

For example, the respiratory line 130 further includes an expiratory branch 132.

Specifically, the at least one gas supply branch 120 is configured to output a gas to the inspiratory branch 131 and an oxygen concentration of the gas in the inspiratory branch 131 can be adjusted by controlling the at least one gas supply branch 120 to output a gas to the inspiratory branch 131.

For example, the medical ventilation system 100 further includes a gas control device 140. The gas control device 140 may control the at least one gas supply branch 120 to output a gas to the inspiratory branch 131 to control the gas which is outputted to the inspiratory branch 131, such controlling includes controlling one or more of: type, flow rate, concentration or pressure of the gas. Of course, by controlling the output a gas of the gas supply branch 120, the gas control device 140 can also provide respiratory support to the patient who is connected to the respiratory line 130.

For example, the oxygen sensor 10 is electrically connected to the gas control device 140 and can transmit oxygen concentration data of the inspiratory branch 131 to the gas control device 140.

For example, air can be outputted to the inspiratory branch 131 through one gas source interface 110 by its gas supply branch 120, while pure oxygen can be outputted to the inspiratory branch 131 through another gas source interface 110 by its gas supply branch 120.

For example, the gas control device 140 may control open degree of at least one gas supply branch 120 to adjust the oxygen concentration of the gas which is outputted to the inspiratory branch 131.

The inventor of the present application found that, the current calibration method for an oxygen sensor usually includes steps of placing the oxygen sensor in a gas environment with a known concentration, waiting for the output voltage of the oxygen sensor to stabilize, recording the corresponding voltage value, and then changing the gas environment to another known concentration, waiting for the output voltage to stabilize again, recording the corresponding voltage value; and then drawing the voltage-oxygen concentration curve according to the two measurement results. The environment of 100% pure oxygen concentration and the environment of 21% pure air are selected as the normal calibration points to obtain the voltage-oxygen concentration curve, so that the concentration value corresponding to each voltage value can be obtained to detect the oxygen concentration of the mixed gas. However, it usually takes 3 to 5 minutes or even longer for the oxygen sensor to output a stable voltage after entering a gas environment of a certain oxygen concentration, so the calibration takes a long time.

Figure 3:
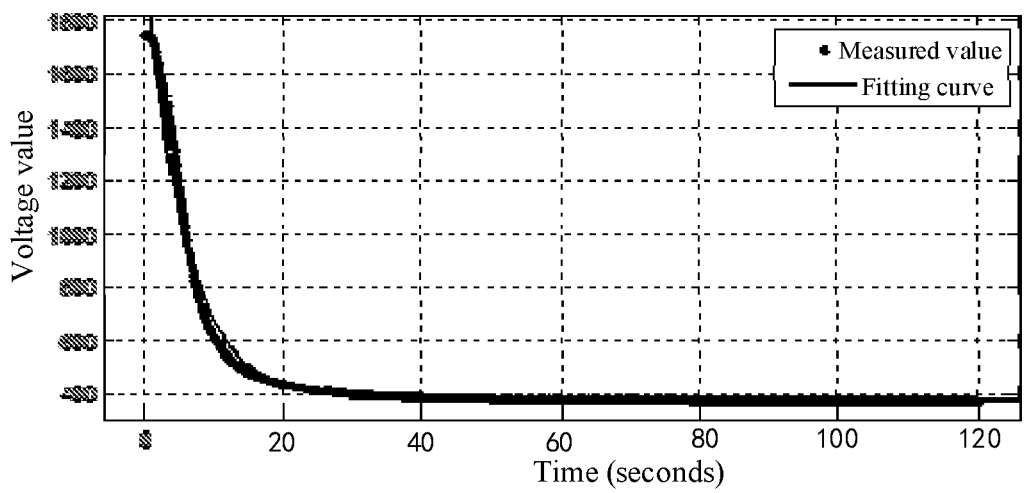
FIG. 3 is a schematic diagram showing a change of output voltage values after an ambient oxygen concentration of a position where the oxygen sensor is located, changes.

For example, as shown in FIG. 3, when the oxygen sensor is moved from pure oxygen environment to pure air environment, its output voltage value drops rapidly in the form of analogous exponential curve, and then gradually stabilizes. The fitting curve can be obtained by fitting the measured voltage outputted by the oxygen sensor at each time point after moving the oxygen sensor to the pure air environment. According to this curve, it can be concluded that the voltage value decreases slowly even at about 120 seconds. If the voltage value at this time is used as the output reference voltage of the oxygen sensor in 21% oxygen environment during calibration, the oxygen concentration monitored in real time is overestimated. Therefore, one method is to wait for 3 minutes or more at each reference concentration when calibrating the oxygen sensor to reduce this deviation.

In view of this discovery, this disclosure proposes a calibration method for a characteristic curve of an oxygen sensor.

As shown in FIG. 1, the calibration method for an oxygen sensor in an embodiment of this disclosure includes steps S110 to S140.

In step S110, at least two electrical signals, which are correspondingly outputted by the oxygen sensor at at least two time points within a preset time period, are acquired, when the oxygen sensor is in a preset oxygen concentration.

For example, the ambient oxygen concentration of a position, where the oxygen sensor is located, is adjusted to a known preset oxygen concentration at a certain time, wherein the certain time can be referred to as a reference time.

For example, the preset oxygen concentration may be, for example, the oxygen concentration of air, such as placing the oxygen sensor in an air environment.

For example, the preset oxygen concentration may be 21% or 100% (pure oxygen), for example. Of course, the specific value of the preset oxygen concentration may not be limited to this.

For example, the oxygen sensor is connected to a detection circuit, which is configured to detect an electrical signal which is outputted by the oxygen sensor, such as a voltage value, current value, etc. For example, the electrical signal can also be a digital value obtained through an analog-to-digital conversion.

For example, after the oxygen sensor is in the preset oxygen concentration at the reference time, the change of the outputted electrical signal (such as the voltage value) with time is shown in FIG. 3.

For example, the electric signals, which are outputted by the oxygen sensor, are detected at least two time points within a preset time period, after the ambient oxygen concentration of a position, where the oxygen sensor is located, is adjusted to a known preset oxygen concentration. As shown in FIG. 3, the electrical signals, which are outputted by the oxygen sensor between the 5th and 40th seconds, can be detected. Optionally, the electrical signals, which are outputted by the oxygen sensor at the 5th, 10th, 20th and 35th seconds, can be detected. Optionally, the electrical signals, which are outputted by the oxygen sensor between the 3rd to 5th seconds and between the 13th to 15th seconds, can be detected.

It can be understood that the time points for detecting the electrical signals, which are outputted by the oxygen sensor, within the preset time period can be discrete, continuous, or a combination of several time periods.

In some embodiments, the duration of the preset time period is no more than two minutes. Therefore, the detection of oxygen sensor can occupy less time and improve the calibration efficiency.

For example, the preset time period is within a time range from the 0th second to the 60th second when the oxygen sensor starts to be in the preset oxygen concentration. During this time period, the electrical signals which are outputted by the oxygen sensor have obvious changes.

Though detecting the outputs of the oxygen sensor at some or all times of this time period, the response function of the oxygen sensor which corresponds to the preset oxygen concentration can be more accurately determined according to the at least two electrical signals.

In some embodiments, the oxygen sensor can be placed inside an ambient environment of the preset oxygen concentration to acquire at least two electrical signals which are correspondingly outputted at at least two time points within the preset time period.

The method for adjusting the ambient oxygen concentration may be to change the position of the oxygen sensor, such as removing it from the machine and placing it inside an ambient environment with a known oxygen concentration. For example, the oxygen sensor can be placed in a pure oxygen environment or an air environment, and then at least two electrical signals which are correspondingly outputted at at least two time points within a preset time period can be detected. For example, the electrical signal level of the electrochemical response which is outputted by the oxygen sensor for a subsequent time period can be recorded.

In other embodiments, a gas with a preset oxygen concentration can be injected into the space where the oxygen sensor is located, and at least two electrical signals which are correspondingly outputted at at least two time points within a preset time period can be acquired.

For example, a chamber, where the oxygen sensor is located, is flushed by a gas with a preset oxygen concentration, to adjust the ambient oxygen concentration of the chamber where the oxygen sensor is located to a known preset oxygen concentration.

For example, acquiring at least two electrical signals, which are correspondingly outputted by the oxygen sensor at at least two time points within a preset time period, when the oxygen sensor is in a preset oxygen concentration, includes filling the inspiratory branch with a gas of the preset oxygen concentration, and acquiring the at least two electrical signals which are correspondingly outputted by the oxygen sensor at the at least two time points within the preset time period.

As shown in FIG. 2, the oxygen sensor 10 is arranged at the inspiratory branch 131 of the medical ventilation system 100. The ambient oxygen concentration of the oxygen sensor 10 can be adjusted to the known preset oxygen concentration by filling the inspiratory branch 131 with a gas of a preset oxygen concentration, such as filling pure oxygen or pure air, into the inspiratory branch of the anesthetic machine or ventilator.

In some embodiments, as shown in FIG. 2, the oxygen concentration of the gas which is outputted from the at least one gas supply branch to the inspiratory branch can be controlled by the gas control device of the medical ventilation system. For example, the gas supply branch that transmits air, can be controlled by the gas control device to transmit air to the inspiratory branch, or the gas supply branch that transmits pure oxygen, can be controlled by the gas control device to transmit pure oxygen to the inspiratory branch.

In step S120, a response function of the oxygen sensor, which corresponds to the preset oxygen concentration, is determined according to the at least two time points and the at least two electrical signals.

Specifically, the response function represents a relationship between the electrical signal, which is outputted by the oxygen sensor, and time.

For example, the response function of the oxygen sensor, which corresponds to the preset oxygen concentration, can be fitted, according to the at least two electrical signals, which are correspondingly outputted by the oxygen sensor at the at least two time points within the preset time period, when the oxygen sensor is in the preset oxygen concentration. According to the response function, an electric signal value which is stably outputted by the oxygen sensor at this oxygen concentration can be determined.

For example, the response function of the oxygen sensor in the preset oxygen concentration can be determined by a nonlinear fitting algorithm, such as a particle swarm optimization algorithm with a compression factor, and the likes.

In some embodiments, as shown in FIG. 4, the step S120 of determining a response function of the oxygen sensor which corresponds to the preset oxygen concentration, according to the at least two time points and the at least two electrical signals, further includes step S121 and step S122.

In step S121, a model parameter of the response function of the oxygen sensor which corresponds to the preset oxygen concentration, can be determined according to the at least two time points and the at least two electrical signals.

Specifically, a response function with a model parameter which is to be determined, can be preset as a function model of the oxygen sensor in the preset oxygen concentration, and then the model parameter can be determined according to the at least two time points and the electrical signal at each time point obtained in step S110, so that the model parameter of the response function of the oxygen sensor in the preset oxygen concentration can be obtained.

The calibration of the oxygen sensor needs to be based on the stable electrical signal which is outputted by the oxygen sensor in the known oxygen concentration, such as the electrical signal which is detected after the oxygen sensor is placed in the known oxygen concentration for 5 minutes. Therefore, the function value of the response function approaches a stable value when the time approaches positive infinity.

In step S122, the response function of the oxygen sensor which corresponds to the preset oxygen concentration is obtained according to the determined model parameter.

In some embodiments, the response function may include one or a superposition of any of: a step response function, an exponential function, or a polynomial function.

It can be understood that the response function is not limited to the above, but can also be functions other than the step response function, exponential function and polynomial function. When time t=0, the function value f (0) of this response function can be used as an initial value, and when t approaches $+\infty$, the function value f ($+\infty$) approaches a fixed value.

For example, the response function may include a step response function. The function model can be used to describe the step response of the oxygen sensor. When the ambient oxygen concentration has a steplike change, the output voltage of the oxygen sensor changes gradually from the initial value to the final stable value under the current known oxygen concentration. The function model f(t) has the following features. When t=0, f (0) represents an electrical signal at the reference time, such as a voltage, when time t approaches $+\infty$, f ($+\infty$) approaches a fixed value, such as the final stable voltage value. For example, f ($+\infty$) can be used as the electrical signal which corresponds to the oxygen sensor under the current known oxygen concentration, such as an output voltage.

For example, the response function may include an exponential function. One possible form is that the response function of the oxygen sensor which outputs the electrical signal under the current known oxygen concentration $f(t)= A+B \times e^{(b/t)}$. Wherein t represents time; A, B and b respectively represents coefficients of the exponential function. According to the at least two time points and the electrical signal at each time point obtained in step S110, such as the coefficients of the exponential function A, B and b which are fitted by the voltage-time curve actually measured within the preset time period, the stable output voltage of the oxygen sensor under the known oxygen concentration can be obtained. When t=0, f (0)=A, that is, the initial output voltage of the oxygen cell. When t approaches $+\infty$, f ($+\infty$) approaches a fixed value, A+B, that is the final stable output voltage of the known oxygen concentration. In the exponential response of oxygen sensor with increased oxygen concentration, b, as well as B, is a positive number. In the exponential of the oxygen sensor with decreased oxygen concentration, b, as well as B, is a negative number.

For example, the response function may include a polynomial function. One possible form is that the response function of the oxygen sensor which outputs the electrical signal under the current known oxygen concentration $f(t)= A_0 + A_1 \cdot 1/t + A_2 \cdot (1/t)^2 + \ldots + A_n \cdot (1/t)^n$. Wherein t represents time, $A_n$ represent coefficients of the polynomial function. According to the at least two time points and the electrical signal at each time point obtained in step S110, such as the voltage-time curve actually measured within the preset time period, coefficients of the polynomial function $A_n$ are fitted and then the stable output voltage of the oxygen sensor under the known oxygen concentration can be obtained. When t=0, $f(0)=A_0$, which represents an output voltage of the oxygen sensor at the reference time, when time t approaches $+\infty$, f ($+\infty$) approaches a fixed value.

In step 130, a steady-state output value of the oxygen sensor in the preset oxygen concentration, is determined according to the response function.

Obtaining the response function by fitting the electrical signals of the oxygen sensor in the preset time period when the oxygen sensor is in the preset oxygen concentration, can reflect a change trend of the output electrical signal when the oxygen sensor is in the preset oxygen concentration. Thus, the output electrical signals of the oxygen sensor when it is in the preset oxygen concentration for 3 minutes, 5 minutes or more can be inferred and these output electrical signals can be used as the steady-state output value.

For example, the function value which determines that the response function approaches be stable is the steady-state output value of the oxygen sensor in the preset oxygen concentration.

In some embodiments, the function value of the response function at a preset time value is determined as the steady-state output value of the oxygen sensor in the preset oxygen concentration.

For example, the preset time value is not less than 3 minutes.

For example, by substituting t=5 minutes into the response function which corresponds to the preset oxygen concentration determined in step S120, the output electrical signal when the oxygen sensor is in the preset oxygen concentration for 5 minutes can be obtained, and this output electrical signal can be taken as the steady-state output value.

In other embodiments, when the time value approaches positive infinity, the function value of the response function is determined as the steady-state output value of the oxygen sensor in the preset oxygen concentration.

For example, when t approaches $+\infty$, the function value $f(+\infty)$ of the response function $f(t)$ is determined as the steady-state output value.

In other embodiments, the steady-state output value can also be determined by the change trend of the function value of the response function. For example, when the change of the function value of the response function at a preset time interval is less than a preset threshold, the function value at the end of the time interval, is determined as the steady-state output value of the oxygen sensor in the preset oxygen concentration.

Thus, the stable electrochemical response level of the oxygen sensor in this oxygen concentration environment can be estimated by using the electrochemical response curve of the oxygen sensor which is fitted in the preset time period after the ambient oxygen concentration changes.

Specifically, a calibration point of the oxygen sensor can be determined according to the steady-state output value of the oxygen sensor in the preset oxygen concentration. For example, if the steady-state output value of the oxygen sensor at 21% oxygen concentration is Q21, the calibration point 1 as shown in FIG. 5 can be determined. If the steady-state output value of the oxygen sensor at 100% oxygen concentration is Q100, the calibration point 2 in FIG. 5 can be determined.

In Step S140, a characteristic curve of the oxygen sensor is determined, according to the steady-state output value of the oxygen sensor in the preset oxygen concentration.

In some embodiments, the preset oxygen concentration may include at least two different oxygen concentrations, and the characteristic curve of the oxygen sensor is determined according to calibration points which are obtained under different oxygen concentrations. At this time, determining a characteristic curve of the oxygen sensor, according to the steady-state output value of the oxygen sensor in the preset oxygen concentration in step S140, may include:

determining the characteristic curve of the oxygen sensor according to at least two calibration points, wherein the at least two calibration points are respectively determined by the steady-state output value which corresponds to the at least two preset oxygen concentrations.

Preferably, determining a characteristic curve of the oxygen sensor, according to the steady-state output value of the oxygen sensor in the preset oxygen concentration in step S140, may include: determining the characteristic curve of the oxygen sensor according to at least two calibration points by linear interpolation; or determining a slope of the characteristic curve according to at least two calibration points, and then determining a point-slope equation of the characteristic curve according to the slope and one calibration point; or determining an intercept equation, an slope-intercept equation, a two-point equation, etc., of the characteristic curve according to at least two calibration points.

For example, the calibration method for an oxygen sensor may include:

acquiring, respectively, at least two electrical signals, which are correspondingly outputted by the oxygen sensor at at least two time points within a preset time period, when the oxygen sensor is in at least two preset oxygen concentrations;

determining a response function of the oxygen sensor which corresponds to the at least two preset oxygen concentrations, according to the at least two time points and the at least two electrical signals;

determining steady-state output values of the oxygen sensor in the at least two preset oxygen concentrations, according to the response function which corresponds to the at least two preset oxygen concentrations;

determining a characteristic curve of the oxygen sensor according to at least two calibration points, wherein the at least two calibration points are respectively determined by the steady-state output values which correspond to the at least two preset oxygen concentrations.

For example, as shown in FIG. 5, the characteristic curve of the oxygen sensor in FIG. 5 can be determined according to the calibration point 1 which is determined by the steady-state output value Q21 of the oxygen sensor in 21% oxygen concentration and the calibration point 2 which is determined by the steady-state output value Q100 of the oxygen sensor in 100% oxygen concentration. For example, the higher the oxygen concentration in the environment where the oxygen sensor is located, the higher the outputted electrical signal, as well as, the outputted voltage value. Accordingly, by detecting the electrical signal which is outputted by the oxygen sensor, the oxygen concentration in the current environment where the oxygen sensor is located can be determined.

Thus, the oxygen sensor curve calibration can be realized according to at least two calibration points. For example, the calibration of the oxygen sensor can be realized by respectively calibrating the outputs of the oxygen sensor in the environment of 21% pure air and in the environment 100% pure oxygen concentration are respectively, and then determining the curve of the output electrical signals which correspond to the oxygen sensor under different oxygen concentrations through linear interpolation.

For example, 100% oxygen concentration calibration and 21% oxygen concentration calibration shall be conducted at least once a month.

For example, the characteristic curve of the oxygen sensor can also be determined according to more than two calibration points. For example, the characteristic curve of the oxygen sensor is determined by the least square method to minimize the sum of the distances between the more than two calibration points and the characteristic curve. Through the least square method, the linear or non-linear characteristic curve can be determined by fitting more than two calibration points.

Specifically, a preset characteristic curve function is obtained, which includes several parameters which are to be determined. The values of the parameters can be determined by the least square method to obtain the characteristic curve of the oxygen sensor. The least square fitting aims to minimize the sum of the distances between the more than two calibration points and the characteristic curve which is determined by fitting.

In some embodiments, determining a characteristic curve of the oxygen sensor, according to the steady-state output value of the oxygen sensor in the preset oxygen concentration in step S140, may include:

acquiring a characteristic curve of the oxygen sensor which is to be calibrated; correcting the characteristic curve of the oxygen sensor which is to be calibrated, according to the steady-state output value of the oxygen sensor in the preset oxygen concentration.

Figure 6:
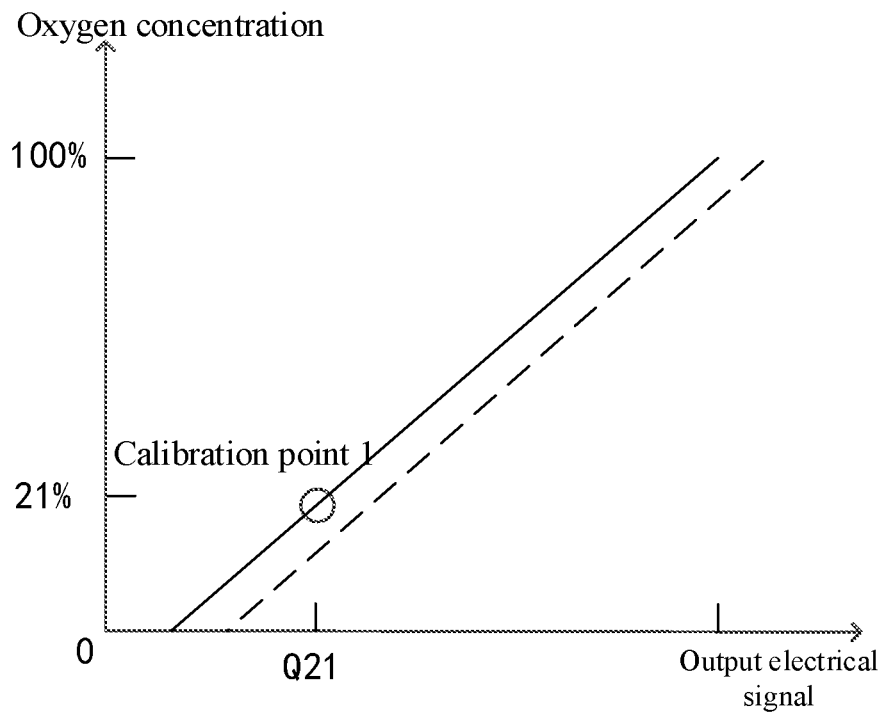
FIG. 6 is a schematic diagram of a modified characteristic curve according to an embodiment.
Figure 7:
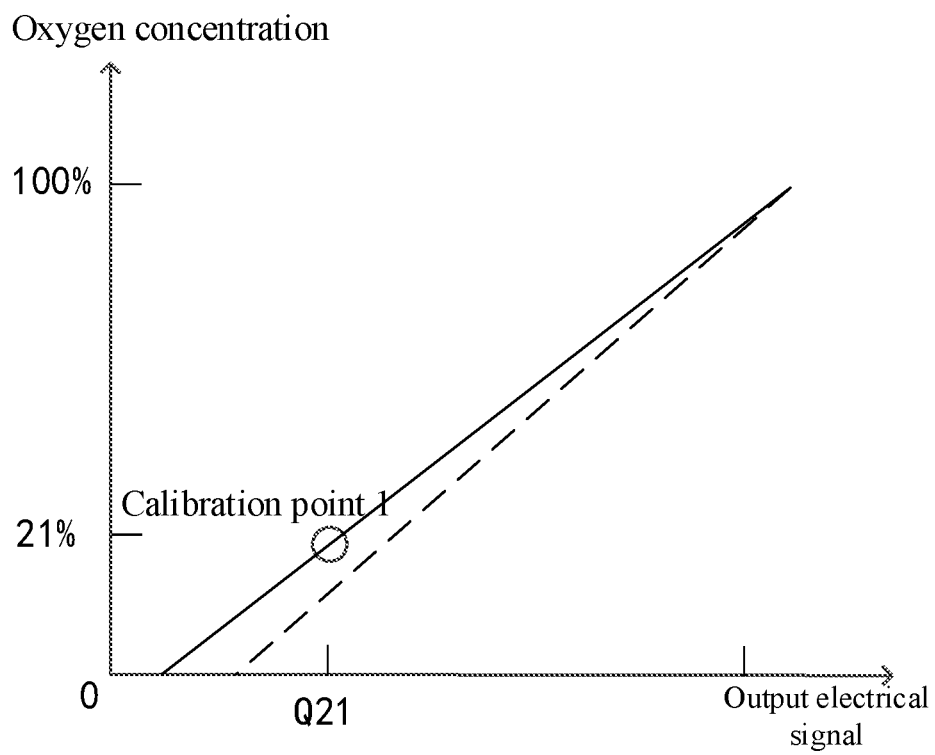
FIG. 7 is a schematic diagram of a modified characteristic curve according to a further embodiment.

For example, as shown in FIG. 6 and FIG. 7, the dotted line in the coordinate axis represents the characteristic curve of the oxygen sensor which is determined at a previous historical time point, such as, the characteristic curve of the oxygen sensor which is determined 72 hours ago. The solid line in the coordinate axis represents the characteristic curve which is corrected according to the calibration point 1 which is recently determined.

For example, correcting the characteristic curve of the oxygen sensor which is to be calibrated, according to the steady-state output value of the oxygen sensor in the preset oxygen concentration, may include:

correcting the characteristic curve which is to be calibrated to enable the corrected characteristic curve to cover at least one calibration point, wherein the calibration point is determined by a corresponding preset oxygen concentration and the steady-state output value which corresponds to the corresponding preset oxygen concentration.

For example, as shown in FIG. 6, the characteristic curve which is to be calibrated can be translated so that the translated characteristic curve covers at least one calibration point.

For example, as shown in FIG. 7, the characteristic curve which is to be calibrated may be rotated so that the rotated characteristic curve covers at least one calibration point. For example, the characteristic curve which is to be calibrated, can be rotated around the calibration point of 100% oxygen concentration. It is understandable that the calibration point of the 100% oxygen concentration can be determined at the previous historical time point.

In some embodiments, the characteristic curve which is to be calibrated may also be corrected according to more than one calibration points. For example, the sum of the distances between the more than one calibration points and the corrected characteristic curve is minimized.

For example, one calibration point is determined at least every 72 hours, such as the calibration point of 21% oxygen concentration, and the characteristic curve of the oxygen sensor is corrected according to the calibration point. For accurate monitoring of daily use, the characteristic curve of 21% oxygen concentration can be corrected every 24 hours.

It can be understood that based on the characteristic curve of the oxygen sensor which is determined in step S140, the oxygen concentration of the environment where the oxygen sensor is located can be determined according to the output electrical signal of the oxygen sensor.

For example, as shown in FIG. 2, the gas control device 140 can detect the output electrical signal of the oxygen sensor in real time, and determine the oxygen concentration of the gas in the inspiratory branch 131 according to the output electrical signal. The gas control device 140 can control a gas flow and/or pressure which is/are outputted from at least one gas supply branch 120, according to the difference between the oxygen concentration and the preset oxygen concentration, so as to adjust the oxygen concentration of the gas which is outputted to the inspiratory branch 131 to reach the preset oxygen concentration.

In the calibration method for an oxygen sensor provided by the embodiment of the disclosure, at least two electrical signals, which are correspondingly outputted by the oxygen sensor at at least two time points within a preset time period when the oxygen sensor is in a preset oxygen concentration, are acquired. Then a response function of the oxygen sensor, which corresponds to the preset oxygen concentration, is determined. As the response function represents a relationship between the electrical signal which is outputted by the oxygen sensor and time, a steady-state output value of the oxygen sensor in the preset oxygen concentration can be determined according to the response function. In this way, a characteristic curve of the oxygen sensor can be determined according to the steady-state output value of the oxygen sensor in the preset oxygen concentration. It is just necessary to acquire at least two electrical signals in a short time after the change of ambient oxygen concentration, then the relationship between the electrical signals outputted by the oxygen sensor and time can be determined. Thus, the electrical signal, which is outputted by the oxygen sensor in a steady state in the corresponding oxygen concentration, can be correspondingly acquired, without waiting a long time for the voltage to be completely stable. Accordingly, the waiting responding time of the oxygen sensor can be reduced, the calibration efficiency can be improved and, it is convenient to improve the oxygen concentration monitoring accuracy of ventilation device, such as anesthetic machine or ventilator.

Figure 8:
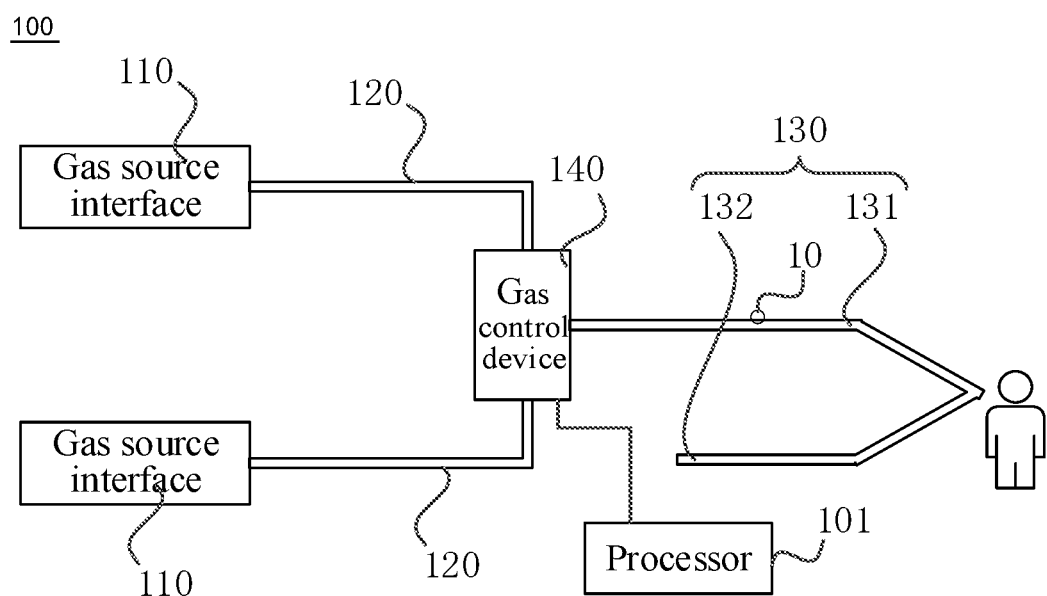
FIG. 8 is a structural diagram of a medical ventilation system in an embodiment.

Please refer to FIG. 8 in combination with the above embodiments. FIG. 8 is a structural diagram of a medical ventilation system in an embodiment which is provided by this disclosure.

The medical ventilation system 100 includes at least one gas source interface 110, at least one gas supply branch 120 which is connected with the at least one gas source interface 110, and a respiratory line 130.

The respiratory line 130 includes an inspiratory branch 131 which is provided with an oxygen sensor 10.

For example, the respiratory line 130 further includes an expiratory branch 132.

Specifically, the at least one gas supply branch 120 is configured to output a gas to the inspiratory branch 131 and an oxygen concentration of the gas in the inspiratory branch 131 can be adjusted by controlling the at least one gas supply branch 120 to output the gas to the inspiratory branch 131.

For example, the medical ventilation system 100 further includes a gas control device 140. The gas control device 140 and the inspiratory branch 131 are respectively connected with the at least one gas supply branch 120. The gas control device 140 may control the at least one gas supply branch 120 to output the gas to the inspiratory branch 131.

For example, air can be outputted to the inspiratory branch 131 through one gas source interface 110 by its corresponding gas supply branch 120, while pure oxygen can be outputted to the inspiratory branch 131 through another gas source interface 110 by its corresponding gas supply branch 120.

For example, the gas control device 140 may control open degree of at least one gas supply branch 120 to adjust the oxygen concentration of the gas which is outputted to the inspiratory branch 131.

Specifically, the medical ventilation system 100 also includes a processor 101, which may be provided, for example, in the gas control device 140 or on a control board other than the gas control device 140.

Specifically, the processor 101 may be a micro controller unit (MCU), a central processing unit (CPU), a digital signal processor (DSP), or the like.

For example, the oxygen sensor 10 is electrically connected with the gas control device 140 and/or the processor 101, and transmits the oxygen concentration data of the inspiratory branch 131 to the gas control device 140 and/or the processor 101.

The processor 101 is configured to perform the steps of the aforementioned calibration method for an oxygen sensor.

For example, the processor 101 configured to perform a computer program which is stored in a memory, and the following steps are implemented when executing the computer program:
controlling at least one gas supply branch to output a gas to the inspiratory branch to adjust an oxygen concentration of gas inside the inspiratory branch;
acquiring at least two electrical signals, which are correspondingly outputted by the oxygen sensor at at least two time points within a preset time period, when the oxygen sensor is in a preset oxygen concentration;
determining a response function of the oxygen sensor which corresponds to the preset oxygen concentration, according to the at least two time points and the at least two electrical signals, wherein the response function represents a relationship between the electrical signal, which is outputted by the oxygen sensor, and time;
determining a steady-state output value of the oxygen sensor in the preset oxygen concentration, according to the response function;
determining a characteristic curve of the oxygen sensor, according to the steady-state output value of the oxygen sensor in the preset oxygen concentration.

As shown in FIG. 8, the oxygen sensor 10 is arranged at the inspiratory branch 131 of the medical ventilation system 100. The ambient oxygen concentration of the position where the oxygen sensor is located, can be adjusted to a known preset oxygen concentration, by filling the inspiratory branch 131 with a gas of a preset oxygen concentration, such as filling pure oxygen or pure air, into the inspiratory branch of the anesthetic machine or ventilator.

For example, the processor 101 or the gas control device 140 may control the open degree of at least one gas supply branch 120 to adjust the oxygen concentration of the gas which is outputted into the inspiratory branch 131.

The specific principle and implementation method of the medical ventilation system provided by the embodiment of this disclosure are similar to the calibration method for an oxygen sensor of the foregoing embodiment, and will not be repeated here.

Another embodiment of the disclosure also provides a ventilator or an anesthetic machine. The ventilator or anesthetic machine includes the above medical ventilation system. The units and implementation methods of the medical ventilation system are described above and will not be repeated here.

The embodiment of this disclosure also provides a computer-readable storage medium, on which a computer program is stored, wherein the computer program includes program instructions, and when the program instructions are executed by a processor, steps of the calibration method for an oxygen sensor are implemented.

The computer-readable storage medium may be an internal storage unit of the medical ventilation system described in any of the preceding embodiments, such as a hard disk or a memory of the medical ventilation system. The computer-readable storage medium can also be an external storage device of the medical ventilation system, such as a plug-in hard disk, smart media card (SMC), secure digital (SD) card, flash card, etc., which are equipped on the medical ventilation system.

In the medical ventilation system, anesthetic machine, and ventilator which are provided in the embodiments of this disclosure, it is just necessary to acquire at least two electrical signals in a short time after the change of ambient oxygen concentration, then the relationship between the electrical signals outputted by the oxygen sensor and time can be determined. Thus, the electrical signal, which is outputted by the oxygen sensor in a steady state in the corresponding oxygen concentration, can be correspondingly acquired, without waiting a long time for the voltage to be completely stable. Accordingly, the waiting responding time of the oxygen sensor can be reduced, the calibration efficiency can be improved and, it is convenient to improve the oxygen concentration monitoring accuracy of ventilation device, such as anesthetic machine or ventilator.

It should be understood that the terms used in this disclosure are only for the purpose of describing specific embodiments and are not intended to limit this disclosure.

It should also be understood that the term "and/or" used in this disclosure and the appended claims refers to any combination of one or more of the items listed in the associated list and all possible combinations, and includes these combinations.

The above description of the disclosed embodiment is only the specific implementation mode of this disclosure, and the protection scope of this disclosure is not limited to this. Various modifications or replacements to these embodiments will be apparent to those skilled in the art, within the technical scope disclosed in this disclosure, and these modifications or replacements should be included in the protection scope of this disclosure. Therefore, the scope of protection of this disclosure shall be subject to the scope of protection of the claims.

What is claimed is:

1. A calibration method for an oxygen sensor electrically connected to a gas control device of a medical ventilation system, comprising:
detecting, by a detection circuit connected to the oxygen sensor, at least two electrical signals, which are correspondingly outputted by the oxygen sensor at at least two time points within a preset time period, when the oxygen sensor is in a preset oxygen concentration;
determining a response function of the oxygen sensor which corresponds to the preset oxygen concentration, according to the at least two time points and the at least two electrical signals, wherein the response function represents a relationship between the electrical signals outputted by the oxygen sensor and the time points;

determining a steady-state output value of the oxygen sensor in the preset oxygen concentration, according to the response function;

determining a characteristic curve of the oxygen sensor, according to the steady-state output value of the oxygen sensor in the preset oxygen concentration; and controlling, by the gas control device, a gas supply in the medical ventilation system according to an actual oxygen concentration determined based on the characteristic curve of the oxygen sensor.

2. The calibration method according to claim 1, wherein acquiring the at least two electrical signals, which are correspondingly outputted by the oxygen sensor at at least two time points within a preset time period, when the oxygen sensor is in a preset oxygen concentration, comprises:

placing the oxygen sensor inside an environment of the preset oxygen concentration to acquire the at least two electrical signals, which are correspondingly outputted by the oxygen sensor at the at least two time points within the preset time period; or filling a space where the oxygen sensor is located with a gas of the preset oxygen concentration to acquire the at least two electrical signals, which are correspondingly outputted by the oxygen sensor at the at least two time points within the preset time period.

3. The calibration method according to claim 1, wherein the oxygen sensor is arranged at an inspiratory branch of a medical ventilation system; and acquiring the at least two electrical signals, which are correspondingly outputted by the oxygen sensor at at least two time points within a preset time period, when the oxygen sensor is in a preset oxygen concentration, comprises:

filling the inspiratory branch with a gas of the preset oxygen concentration, and acquiring the at least two electrical signals, which are correspondingly outputted by the oxygen sensor at the at least two time points within the preset time period.

4. The calibration method according to claim 1, wherein a time duration of the preset time period is no more than two minutes.

5. The calibration method according to claim 1, wherein determining the response function of the oxygen sensor which corresponds to the preset oxygen concentration, according to the at least two time points and the at least two electrical signals, comprises:

determining a model parameter of the response function of the oxygen sensor which corresponds to the preset oxygen concentration, according to the at least two time points and the at least two electrical signals; and obtaining the response function of the oxygen sensor which corresponds to the preset oxygen concentration, according to the determined model parameter.

6. The calibration method according to claim 5, wherein the response function approaches a fixed value when the time approaches positive infinity; or the response function comprises a step response function, an exponential function, or a polynomial function.

7. The calibration method according to claim 5, wherein determining the steady-state output value of the oxygen sensor in the preset oxygen concentration, according to the response function, comprises:

determining a function value of the response function, which approaches a steady state, as the steady-state output value of the oxygen sensor in the preset oxygen concentration.

8. The calibration method according to claim 1, wherein determining the characteristic curve of the oxygen sensor, according to the steady-state output value of the oxygen sensor in the preset oxygen concentration, comprises:

acquiring a characteristic curve of the oxygen sensor which is to be calibrated; and correcting the characteristic curve of the oxygen sensor which is to be calibrated, according to the steady-state output value of the oxygen sensor in the preset oxygen concentration.

9. The calibration method according to claim 8, wherein correcting the characteristic curve of the oxygen sensor which is to be calibrated, according to the steady-state output value of the oxygen sensor in the preset oxygen concentration, comprises:

correcting the characteristic curve which is to be calibrated to enable the corrected characteristic curve to cover at least one calibration point, wherein the calibration point is determined by a corresponding preset oxygen concentration and the steady-state output value which corresponds to the corresponding preset oxygen concentration.

10. The calibration method according to claim 9, wherein the preset oxygen concentration comprises at least two preset oxygen concentrations, and correcting the characteristic curve of the oxygen sensor which is to be calibrated, according to the steady-state output value of the oxygen sensor in the preset oxygen concentration, further comprises:

determining the characteristic curve of the oxygen sensor according to at least two calibration points, wherein the at least two calibration points are respectively determined by the steady-state output values which correspond to the at least two preset oxygen concentrations, respectively.

11. The calibration method according to claim 10, wherein determining the characteristic curve of the oxygen sensor according to at least two calibration points, comprises:

determining the characteristic curve of the oxygen sensor according to the at least two calibration points by linear interpolation.

* * * * *